United States Patent

Boeger et al.

(10) Patent No.: US 6,852,888 B2
(45) Date of Patent: Feb. 8, 2005

(54) CARBOXYLIC ACID DERIVATIVES

(75) Inventors: Manfred Boeger, deceased, late of Weil am Rhein (DE); by Franziska Boeger, legal representative, Weil am Rhein (DE); Peter Maienfisch, Rodersdorf (CH); Thomas Pitterna, Basel (CH); Christian Martin Boeger, Inzlingen (DE); Oliver Wolfang Boeger, Weil am Rhein (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/728,184

(22) Filed: Dec. 2, 2000

(65) Prior Publication Data

US 2003/0216467 A1 Nov. 20, 2003

Related U.S. Application Data

(63) Continuation of application No. PCT/EP99/03790, filed on May 31, 1999.

(30) Foreign Application Priority Data

Jun. 2, 1998 (CH) .............................................. 1195/98

(51) Int. Cl.[7] ...................... C07C 233/09; A01N 37/18
(52) U.S. Cl. ...................................... 564/207; 514/628
(58) Field of Search ........................ 564/207; 514/628

(56) References Cited

FOREIGN PATENT DOCUMENTS

| DE | 019531300 A1 | * 2/1997 |
|----|---|---|
| EP | A 432 861 | 6/1991 |
| EP | A 495 313 | 7/1992 |
| EP | 0 661 289 | 7/1995 |
| EP | A 742 202 | 11/1996 |
| WO | WO 92 15555 | 9/1992 |
| WO | WO 97 08132 | 3/1997 |

* cited by examiner

Primary Examiner—Shailendra Kumar
(74) Attorney, Agent, or Firm—Rose M. Allen

(57) ABSTRACT

There are described compounds of formula

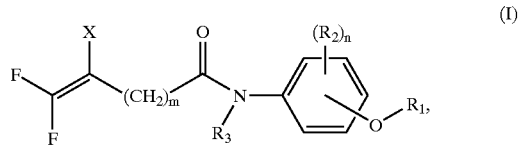

(I)

in free form or in salt form,
a process for the preparation of such compounds and the use of such compounds, pesticidal compositions in which the active ingredient is selected from those compounds, in free form or in an agrochemically suitable salt form, a method of preparing such compositions and the use of such compositions, plant propagation material treated with such compositions, and a method of controlling pests.

7 Claims, No Drawings

CARBOXYLIC ACID DERIVATIVES

This application is a CON of PCT/EP99/03790, filed May 31, 1999.

The present invention relates to a compound of formula

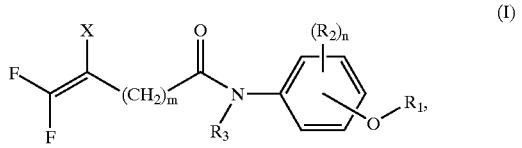

wherein
- $R_1$ is halo-$C_1$–$C_6$alkyl; halo-$C_2$–$C_6$alkenyl; or halo-$C_3$–$C_6$alkynyl;
- $R_2$ is halogen, nitro, cyano, $C_1$–$C_{10}$alkyl, $C_2$–$C_6$alkenyl, $C_2$–$C_6$alkynyl, $C_3$–$C_8$cyclo-alkyl, $C_1$–$C_6$alkoxy, $C_3$–$C_6$alkenyloxy, halo-$C_1$–$C_{10}$alkyl, halo-$C_2$–$C_6$alkenyl, halo-$C_1$–$C_6$alkoxy, $C_3$–$C_6$alkynyloxy, $C_1$–$C_4$alkylthio, di($C_1$–$C_4$-alkyl)amine in which the two alkyl groups are independent of one another; aryl, aryloxy, arylthio, or substituted aryl, aryloxy or arylthio;
- $R_3$ is hydrogen or unsubstituted or substituted $C_1$–$C_{10}$alkyl; or benzyl in which the phenyl ring is unsubstituted or monosubstituted by a substituent selected from the group consisting of nitro, halogen, —$CF_3$, —CN and $C_1$–$C_4$alkyl;
- m is 1, 3, 5, 7 or 9;
- n is 0, 1, 2, 3 or 4; and
- X is hydrogen, fluorine or methyl;
- in free form or in salt form,
- with the proviso that m may not be 1 when X and $R_3$ are hydrogen, n is 0 and —O—$R_1$ is 4-tri-fluoromethoxy;
- to a process for the preparation of such compounds and to the use of such compounds, to pesticidal compositions in which the active ingredient is selected from those compounds, in free form or in an agrochemically suitable salt form, to a method of preparing such compositions and to the use of such compositions, to plant propagation material treated with such compositions, and to a method of controlling pests.

Some halovinylcarboxylic acid derivatives are proposed in the literature as active ingredients in pesticides. The biological properties of those known compounds are not entirely satisfactory in the area of pest control, however, for which reason there is a need to provide further compounds having pest-controlling properties, especially for the control of insects and representatives of the order Acarina. This problem is solved in accordance with the invention by the provision of the present compounds of formula (I).

The compounds of formula (I) are capable of forming salts with bases. Suitable salts with bases are, for example, metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. Within the scope of the invention, preference is given to salts that are advantageous from an agrochemical standpoint, but the invention also includes other salts, which are used, for example, in the isolation or purification of free compounds of formula (I) or agrochemically suitable salts thereof. The expression "compounds of formula (I)" is accordingly to be understood hereinbefore and hereinafter as meaning both the free compounds of formula (I) and salts thereof. In each case the free form is preferred.

The general terms used hereinbefore and hereinafter have the meanings given below unless defined otherwise.

Halogen—as a group per se and as a structural element of other groups and compounds, such as haloalkyl, halocycloalkyl, haloalkenyl, haloalkynyl and haloalkoxy,—is fluorine, chlorine, bromine or iodine, especially fluorine, chlorine or bromine, more especially fluorine or chlorine, especially chlorine.

Unless defined otherwise, carbon-containing groups and compounds each contain from 1 up to and including 20, preferably from 1 up to and including 18, especially from 1 up to and including 10, more especially from 1 up to and including 6, very especially from 1 up to and including 4, more especially from 1 up to and including 3, especially 1 or 2, carbon atoms, with methyl being especially preferred.

Alkyl—as a group per se and as a structural element of other groups and compounds, such as, for example, haloalkyl, alkoxy, alkoxyalkyl, haloalkoxy, alkoxycarbonyl, alkylthio, haloalkylthio, alkylsulfonyl and alkylsulfonyloxy—is, in each case with due consideration being given to the number of carbon atoms present in the group or compound in question, either straight-chain, e.g. methyl, ethyl, n-propyl, n-butyl, n-hexyl, n-octyl, n-decyl, n-dodecyl, n-hexadecyl or n-octadecyl, or branched, e.g. isopropyl, isobutyl, sec-butyl, tert-butyl, isopentyl, neopentyl or isohexyl.

Alkenyl and alkynyl—as groups per se and as structural elements of other groups and compounds, such as haloalkenyl, haloalkynyl, alkenyloxy, haloalkenyloxy, alkynyloxy or haloalkynyloxy—are straight-chain or branched and each contains two unsaturated carbon-carbon bonds or, preferably, one unsaturated carbon-carbon bond. The following may be mentioned by way of example: vinyl, prop-2-en-1-yl, 2-methylprop-2-en-1-yl, but-2-en-1-yl, but-3-en-1-yl, prop-2-yn-1-yl, but-2-yn-1-yl and but-3-yn-1-yl.

Cycloalkyl—as a group per se and as a structural element of other groups and compounds, such as, for example, alkyl—is cyclopropyl, cyclobutyl, cyclopentyl, cyclohexyl, cycloheptyl or cyclooctyl. Cyclopropyl, cyclopentyl and cyclohexyl are preferred.

Halo-substituted carbon-containing groups and compounds, such as haloalkyl and haloalkoxy, may be partially halogenated or perhalogenated, and in the case of polyhalogenation the halogen substituents may be identical or different. Examples of haloalkyl—as a group per se and as a structural element of other groups and compounds, such as haloalkoxy,—are methyl mono- to tri-substituted by fluorine, chlorine and/or bromine, such as $CHF_2$, $CF_3$ or $CH_2Cl$; ethyl mono- to penta-substituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CH_2CH_2Cl$, $CF_2CHBr_2$, $CF_2CHClF$, $CF_2CHBrF$ or $CClFCHClF$; propyl or isopropyl mono- to hepta-substituted by fluorine, chlorine and/or bromine, such as $CH_2CHBrCH_2Br$, $CF_2CHFCF_3$, $CH_2CF_2CF_3$, $CF_2CF_2CF_3$, $CH(CF_3)_2$ or $CH_2CH_2CH_2Cl$; and butyl mono- to nona-substituted by fluorine, chlorine and/or bromine, or an isomer thereof, such as $CF(CF_3)CHFCF_3$, $CF_2(CF_2)_2CF_3$ or $CH_2(CF_2)_2CF_3$.

Aryl is phenyl or naphthyl, with preference being given to phenyl.

The following are preferred embodiments within the scope of the invention:

a) a compound of formula (I) wherein $R_1$ is halo-$C_1$–$C_3$alkyl or halo-$C_3$–$C_6$alkenyl; preferably halo- $C_1$–$C_2$alkyl, especially 2-chloro-1,1,2-trifluoroethyl or 1,1,2,2-tetrafluoroethyl;

b) a compound of formula (I) wherein $R_2$ is halogen or $C_1$–$C_4$alkyl, especially fluorine, chlorine, methyl or isopropyl; more especially methyl or isopropyl; preferably in the 2-position;

c) a compound of formula (I) wherein m is 3;

d) a compound of formula (I) wherein n is 0, 1, 2 or 3; preferably 0, 1 or 2; especially 0 or 1, more especially 1;

e) a compound of formula (I) wherein $R_3$ is hydrogen or $C_1$–$C_4$alkyl, especially hydrogen;

f) a compound of formula (I) wherein X is hydrogen or fluorine, especially hydrogen;

g) a compound of formula (I) wherein —O—$R_1$ is in the 4-position.

Special preference is given within the scope of the invention to the compounds of formula (I) listed in Tables 1 and 2.

The invention relates also to a process for the preparation of compounds of formula (I), in free form or in salt form, which comprises a) reacting a compound of formula

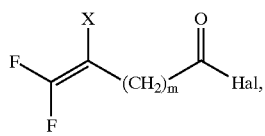

(II)

wherein X and m are as defined for formula (I) and Hal is halogen, preferably chlorine or bromine, where appropriate in an inert solvent and in the presence of an acid-binding agent, with a compound of formula

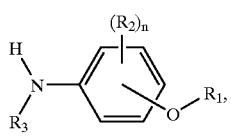

(III)

wherein $R_1$, $R_2$, $R_3$ and n are as defined for formula (I), or, optionally, with a salt thereof, or b) reacting a compound of formula

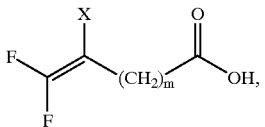

(IV)

wherein X and m are as defined for formula (I), where appropriate in the presence of a condensation agent or a water-removing agent, with a compound of formula (III) or with a salt thereof; or c) reacting a compound of formula

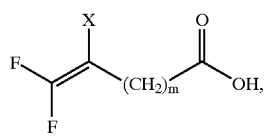

(V)

wherein X and m are as defined for formula (I), with a compound of formula (III) or with a salt thereof;

and/or, if desired, converting a compound of formula (I) obtainable according to the process or in another manner, in free form or in salt form, into a different compound of formula (I), separating a mixture of isomers obtainable according to the process and isolating the desired isomer, and/or converting a free compound of formula (I) obtainable according to the process or in another manner into a salt or converting a salt of a compound of formula (I) obtainable according to the process or in another manner into the free compound of formula (I) or into a different salt.

The starting materials of formulae (II), (III), (IV) and (V) mentioned hereinbefore and hereinafter used for the preparation of the compounds of formula (I) in free form or in salt form are known or can be prepared according to methods known per se.

The reactions described hereinbefore and hereinafter are carried out in a manner known per se, for example in the absence or, where appropriate, in the presence, of a suitable solvent or diluent or a mixture thereof, the reaction being carried out as required with cooling, at room temperature or with heating, for example in a temperature range of from approximately –80° C. to the boiling temperature of the reaction mixture, preferably from approximately –20° C. to approximately +150° C., and, if necessary, in a closed vessel, under pressure, in an inert gas atmosphere and/or under anhydrous conditions. Especially advantageous reaction conditions may be found in the Examples.

The reaction of process a) is preferably carried out in an inert, hydroxy-group-free solvent in the presence of an organic base, such as, for example, pyridine, 4-dimethylaminopyridine, 4-pyrrolidinopyridine, lutidine, collidine, trialkylamine, N,N-dialkylaniline, or in the presence of a bicyclic, non-nucleophilic base, such as 1,4-diazabicyclo[2.2.2]octane (DABCO), 1,5-diazabicyclo[4.3.0]non-5-ene (DBN) or 1,8-diazabicyclo[5.4.0]undec-7-ene (DBU). The reaction is generally carried out at temperatures of from –30° C. to +70° C., preferably from –10° C. to +50° C., and advantageously in the presence of an inert solvent or solvent mixture. Suitable solvents are, for example, aliphatic and aromatic hydrocarbons, such as benzene, toluene, xylenes, petroleum ether, hexane; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert-butyl methyl ether etc.), anisole, dioxane, tetrahydrofuran; nitriles, such as acetonitrile, propionitrile; esters, such as ethyl acetate, propyl acetate or butyl acetate; ketones, such as acetone, diethyl ketone, methyl ethyl ketone or methyl isobutyl ketone; and mixtures of such solvents with one another. The reaction may, however, also be carried out in an excess of one of the above-mentioned bases, or instead of the base a second equivalent or a relatively large excess of the compound of formula (III) may be used. The reaction is carried out under the ambient pressure, although it may also be carried out at elevated or reduced pressure.

In process variant b), the reaction is advantageously carried out in the presence of a condensation agent, such as, for example, phosphorous acid dichloride phenyl ester, benzenephosphonic acid dichloride, 2,4,6-trichloro-s-triazine, carbonic acid diimidazolide, a carbodiimide, such as dicyclohexylcarbodiimide (DCC), aluminium oxide, titanium tetrachloride, 2,2,4,4,6,6-hexachloro-1,3,5-triazatriphosphorin or chloroformic acid lower alkyl esters, such as isobutyl chloroformate. Advantageously, the reaction is carried out in the presence of an inert solvent or solvent mixture at temperatures of from −30° C. to +70° C., preferably from −10° C. to +50° C. The reaction is preferably carried out in the presence of a base, such as, for example, in the presence of an organic amine, such as a trialkylamine (trimethylamine, triethylamine, triisopropylamine or diisopropylethylamine), a pyridine (pyridine itself, 4-dimethylaminopyridine or 4-pyrrolidinopyridine), a morpholine (N-methylmorpholine) or an N,N-dialkylaniline (N,N-dimethylaniline or N-methyl-N-ethyl-aniline). Suitable solvents for the reaction are, for example, aliphatic and aromatic hydrocarbons, such as benzene, toluene, xylenes, petroleum ether, hexane; halogenated hydrocarbons, such as chlorobenzene, methylene chloride, ethylene chloride, chloroform, carbon tetrachloride, tetrachloroethylene; ethers, such as dialkyl ethers (diethyl ether, diisopropyl ether, tert-butyl methyl ether etc.), anisole, dioxane, tetrahydrofuran; nitriles, such as acetonitrile, propionitrile; esters, such as ethyl acetate, propyl acetate or butyl acetate; and mixtures of such solvents with one another.

In process variant c), the reactions are advantageously carried out in the presence of an inert solvent or solvent mixture at temperatures of from 0° to +120° C., preferably from 50° C. to +100° C. Suitable solvents are the same as those mentioned under variant a).

Compounds of formula (I) obtainable according to the process or in another manner may be converted in a manner known per se into different compounds of formula (I) by replacing one or more substituents of the starting compound of formula (I) by one or more other substituents according to the invention in customary manner.

Depending on the choice of the reaction conditions and starting materials suitable for the case in question, it is possible in a reaction step for only one substituent to be replaced by another substituent according to the invention, or it is possible for several substituents to be replaced by other substituents according to the invention in the same reaction step.

Salts of compounds of formula (I) can be prepared in a manner known per se. For example, salts of compounds of formula (I) with bases are obtained by treating the free compounds with a suitable base or with a suitable ion exchange reagent.

Salts of compounds of formula (I) can be converted into the free compounds of formula (I) in customary manner, for example by treatment with a suitable acid or with a suitable ion exchange reagent.

Salts of compounds of formula (I) can be converted into different salts of a compound of formula (I) in a manner known per se.

Depending on the procedure and on the reaction conditions, the compounds of formula (I) having salt-forming properties may be obtained in free form or in the form of salts.

The compounds of formula (I) in free form or in salt form may be in the form of one of the possible isomers or in the form of a mixture thereof; for example depending on the number of asymmetric carbon atoms occurring in the molecule and the absolute and relative configuration thereof and/or depending on the configuration of non-aromatic double bonds occurring in the molecule, they may be in the form of pure isomers, such as antipodes and/or diastereoisomers, or in the form of mixtures of isomers, such as mixtures of enantiomers, e.g. racemates, mixtures of diastereoisomers or mixtures of racemates. The invention relates both to the pure isomers and to all possible mixtures of isomers and is to be interpreted as such hereinbefore and hereinafter, even if stereochemical details are not specifically mentioned in every case.

Mixtures of diastereoisomers, mixtures of racemates and mixtures of double-bond isomers of compounds of formula (I) in free form or in salt form, obtainable according to the process—depending on the starting materials and procedures chosen—or in another manner, can be separated in known manner into the pure diastereoisomers or racemates on the basis of the physicochemical differences between their constituents, for example by fractional crystallisation, distillation and/or chromatography.

Mixtures of enantiomers, such as racemates, obtainable in a corresponding manner can be resolved into the optical antipodes according to known methods, for example by recrystallisation from an optically active solvent, by chromatography on chiral adsorbents, for example high pressure liquid chromatography (HPLC) on acetyl cellulose, with the aid of suitable microorganisms, by cleavage with specific, immobilised enzymes, via the formation of inclusion compounds, for example using chiral crown ethers, in which case only one enantiomer is complexed, or by conversion into diastereoisomeric salts and separation of the mixture of diastereoisomers so obtained, for example on the basis of their different solubilities by means of fractional crystallisation, into the diastereoisomers from which the desired enantiomer can be freed by the action of suitable agents.

Apart from being obtained by separation of corresponding mixtures of isomers, it is also possible for pure diastereoisomers and enantiomers to be obtained according to the invention by generally known methods of diastereoselective or enantioselective synthesis, for example by carrying out the process according to the invention using starting materials that have correspondingly suitable stereochemistry.

Where the individual components have different biological activities, in each case it is advantageous to isolate or synthesise the biologically more active isomer, e.g. enantiomer or diastereoisomer, or mixture of isomers, e.g. mixture of enantiomers or mixture of diastereoisomers.

The compounds of formula (I) in free form or in salt form may also be obtained in the form of their hydrates and/or may include other solvents, for example solvents that may have been used for the crystallisation of compounds that occur in solid form.

The invention relates to all those embodiments of the process according to which a compound obtainable as starting material or intermediate at any stage of the process is used as starting point and all or some of the remaining steps are carried out, or according to which a starting material is used in the form of a derivative or salt and/or a racemate or antipode or, especially, is formed under the reaction conditions.

In the process of the present invention the starting materials and intermediates used, each in free form or in salt form, are preferably those which result in the compounds of formula (I) described at the outset as being especially valuable or salts thereof.

The invention relates especially to the preparation process described in Example P1.

In the area of pest control, while being well tolerated by warm-blooded animals, fish and plants, the compounds of formula (I) according to the invention, even at low rates of concentration, are valuable preventive and/or curative active ingredients having a very advantageous biocidal spectrum. The compounds according to the invention are effective against all or individual development stages of normally sensitive animal pests and also resistant animal pests, such as insects or representatives of the order Acarina. The insecticidal or acaricidal action of the compounds according to the invention may manifest itself directly, that is to say in the death of the pests, which occurs immediately or only after some time, for example during moulting, or indirectly, for example in reduced oviposition and/or hatching rate, good activity corresponding to a mortality rate of at least 50 to 60%.

The mentioned animal pests include, for example, those mentioned in European Patent Application EP-A-736 252. The pests mentioned therein are accordingly included in the subject of the present invention by reference. The compounds according to the invention are suitable especially in the control of *Boophilus microplus, Nilaparvata lugens* and *Tetranychus urticae*, and preferably in the control of those pests in vegetable, fruit and rice crops.

With the compounds according to the invention it is possible to control, that is to say inhibit or destroy, pests of the type mentioned that occur especially on plants, more especially on useful plants and ornamentals in agriculture, horticulture and forestry, or on parts of plants, such as fruit, blossom, leaves, stems, tubers or roots, while the parts of plants that grow later are also protected against those pests to some extent.

Target crops include especially cereals, such as wheat, barley, rye, oats, rice, maize and sorghum; beet, such as sugar beet and fodder beet; fruit, for example pomes, stone fruit and soft fruit, such as apples, pears, plums, peaches, almonds, cherries and berries, e.g. strawberries, raspberries and blackberries; leguminous fruits, such as beans, lentils, peas and soybeans; oil plants, such as rape, mustard, poppy, olives, sunflowers, coconut, castor oil plants, cocoa beans and groundnuts; cucurbitaceae, such as marrows, cucumbers and melons; fibre plants, such as cotton, flax, hemp and jute; citrus fruit, such as oranges, lemons, grapefruit and mandarins; vegetables, such as spinach, lettuce, asparagus, cabbages, carrots, onions, tomatoes, potatoes and paprika; lauraceae, such as avocados, cinnamon and camphor; and also tobacco, nuts, coffee, aubergines, sugar cane, tea, pepper, vines, hops, bananas, natural rubber plants and ornamentals.

Further areas of use of the compounds according to the invention are the protection of stored goods and stocks and of materials and in the hygiene sector, especially the protection of domestic animals and livestock against pests of the type mentioned.

The invention accordingly relates also to pesticidal compositions, such as emulsifiable concentrates, suspension concentrates, directly sprayable or dilutable solutions, coatable pastes, dilute emulsions, wettable powders, soluble powders, dispersible powders, wettable powders, dusts, granules or encapsulations in polymeric substances, which comprise at least one of the compounds according to the invention, the type of formulation being chosen in accordance with the intended objectives and the prevailing circumstances.

The active ingredient is used in those compositions in pure form, a solid active ingredient being used, for example, in a specific particle size, or, preferably, together with at least one of the adjuvants customary in formulation technology, such as extenders, e.g. solvents or solid carriers, or surface-active compounds (surfactants).

Suitable formulation adjuvants are, for example, solid carriers, solvents, stabilisers, slow-release adjuvants, dyes and optionally surface-active substances (surfactants). Suitable carriers and adjuvants in this case include all substances customarily used in crop protection products, especially in products for controlling snails and slugs. Suitable adjuvants, such as solvents, solid carriers, surface-active compounds, non-ionic surfactants, cationic surfactants, anionic surfactants and further adjuvants in the compositions used in accordance with the invention are, for example, the same as those described in EP-A-736 252; they are included in the subject of the present invention by reference.

The compositions usually contain from 0.1 to 99%, especially from 0.1 to 95%, of active ingredient and from 1 to 99.9%, especially from 5 to 99.9%, of at least one solid or liquid adjuvant, it generally being possible for from 0 to 25%, especially from 0.1 to 20%, of the composition to be surfactants (in each case percentages are by weight). Whereas commercial products will preferably be formulated as concentrates, the end user will normally employ dilute formulations which have considerably lower concentrations of active ingredient. Preferred formulations have especially the following composition (%=percent by weight):

| Emulsifiable concentrates: | |
|---|---|
| active ingredient: | 1 to 95%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granules: | |
| active ingredient: | 0.5 to 30%, preferably 3 to 15% |
| solid carrier: | 99.5 to 70%, preferably 97 to 85% |

The activity of the compositions according to the invention can be substantially broadened and adapted to prevailing circumstances by the addition of other insecticidal active ingredients. Examples of suitable additional active ingredients include, for example, representatives of the following classes of active ingredient: organophosphorus compounds, nitrophenols and derivatives, formamidines, acylureas, carbamates, pyrethroids, nitroenamines and derivatives, pyrroles, thioureas and derivatives, chlorinated hydrocarbons and *Bacillus thuringiensis* preparations. The compositions according to the invention may also comprise other solid or liquid adjuvants, such as stabilisers, for example vegetable oils or epoxidised vegetable oils (e.g. epoxidised coconut oil, rapeseed oil or soybean oil), antifoams, e.g. silicone oil, preservatives, viscosity regulators, binders and/or tackifiers, as well as fertilisers or other active ingredients for obtaining special effects, e.g. acaricides, bactericides, fungicides, nematocides, molluscicides or selective herbicides.

The compositions according to the invention are prepared in known manner: in the absence of adjuvants, for example, by grinding, sieving and/or compressing a solid active ingredient or active ingredient mixture, for example to a specific particle size, and, in the presence of at least one adjuvant, for example, by intimately mixing and/or grinding the active ingredient or active ingredient mixture with the adjuvant(s). The invention relates also to those methods of preparing the compositions according to the invention and to the use of compounds I in the preparation of such compositions.

The invention relates also to the methods of applying the compositions, that is the methods of controlling pests of the type mentioned, such as spraying, atomising, dusting, coating, dressing, scattering or pouring, which are chosen in accordance with the intended objectives and the prevailing circumstances, and to the use of the compositions in the control of pests of the type mentioned. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of crop protection is application to the leaves of the plants (foliar application), the frequency and rate of application depending on the risk of infestation by the pest in question. The active ingredient may, however, also penetrate the plants through the root system (systemic action) as a result of impregnation of the locus of the plant with a liquid formulation or by incorporation of the active ingredient in solid form, for example in the form of granules, in the locus of the plant, for example in the soil (soil application). In the case of paddy rice crops, such granules may be applied in metered amounts to the flooded rice field.

The compositions according to the invention are suitable also for the protection of plant propagation material, including genetically modified propagation material, e.g. seed, such as fruit, tubers or grains, or plant cuttings, against animal pests. The propagation material may be treated with the composition before planting, for example seed may be dressed before sowing. The compounds according to the invention may also be applied to seed grains (coating) either by impregnating the grains with a liquid formulation or by coating them with a solid formulation. The composition may also be applied to the planting site when the propagation material is being planted, for example may be applied to the seed furrow during sowing. The invention relates also to that method of treating plant propagation material and to the plant propagation material so treated.

The following Examples serve to illustrate the invention but do not limit the invention. Temperatures are given in degrees Celsius, and solvent mixing ratios are quoted in parts by volume.

PREPARATION EXAMPLES

Example P1

Preparation of 6,6-difluorohex-5-enoic Acid [4-(2-chloro-1,1,2-trifluoroethoxy)-2-methylphenyl]amide of Formula

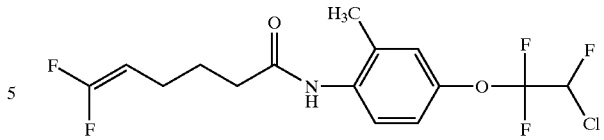

a) [4-(2-chloro-1,1,2-trifluoroethoxy)-2-methyl-1-nitrobenzene of formula

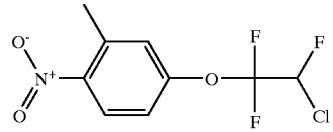

253.4 g of chlorotrifluoroethylene are introduced at room temperature into 157.8 g of 3-methyl-4-nitrophenol and 76.6 g of potassium hydroxide powder in 750 ml of dimethylformamide, in the course of which the temperature is not allowed to exceed 60° C. The reaction mixture is then poured into 4 litres of ice-water and extracted with toluene. After drying the toluene phase with sodium sulfate, the solvent is concentrated by evaporation, yielding 266 g of the title compound (oil).

b) [4-(2-Chloro-1,1,2-trifluoroethoxy)-2-methylphenyl]amine of formula

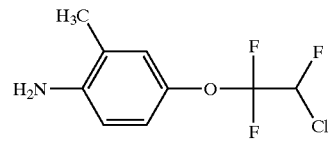

266.0 g of 4-(2-chloro-1,1,2-trifluoroethoxy)-2-methyl-1-nitrobenzene in dioxane are reacted with hydrogen, at room temperature, in the presence of 20 g of Raney nickel. After removal of the catalyst, the solvent is concentrated by evaporation and the residue is distilled under a high vacuum, yielding the title compound in the form of an oil.

c) 6,6-Difluorohex-5-enoic acid [4-(2-chloro-1,1,2-trifluoroethoxy)-2-methylphenyl]amide: 155.4 g of 6,6-difluorohex-5-enoic acid chloride are added dropwise to 204.5 g of [4-(2-chloro-1,1,2-trifluoroethoxy)-2-methylphenyl]amine, 142.5 ml of triethylamine and 5 g of N,N-dimethylaminopyridine stirred at room temperature in 2 litres of toluene; during the course of the addition, the temperature is maintained at approximately 20° C. by cooling with ice. The reaction mixture is then stirred overnight at room temperature and washed once with sodium hydrogen carbonate solution and once with water, and the organic phase is dried over sodium sulfate. After concentration of the solvent by evaporation, the reaction product is precipitated by the addition of hexane. After suction-filtering, the solid, brown filtration residue is taken up in ethyl acetate and purified on silica gel (eluant: ethyl acetate/hexane (1:1)). The title compound, having a melting point of 59–60° C. (compound 1.1), is obtained.

Example P2

The further compounds of Tables 1 and 2 can be prepared in a manner analogous to that described above:

TABLE 1

Compounds of formula

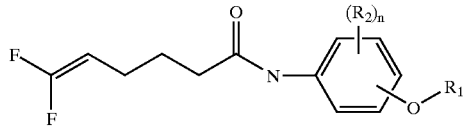

| Example No. | $R_1$ | $(R_2)_n$ | Phys. data |
|---|---|---|---|
| 1.1 | 4-OCF$_2$CHClF | 2-methyl | m.p.: 59–60° C. |
| 1.2 | 4-OCF$_2$CHFCF$_3$ | n = 0 | m.p.: 82–83° C. |
| 1.3 | 4-OCF$_2$CHF$_2$ | n = 0 | m.p.: 103–104° C. |
| 1.4 | 4-OCF$_2$CHF$_2$ | 2-isopropyl | m.p.: 63–64° C. |
| 1.5 | 4-OCF$_2$CHF$_2$ | 2-methyl | m.p.: 59–60° C. |
| 1.6 | 4-OCF$_3$ | n = 0 | m.p.: 67–68° C. |
| 1.7 | 4-OCF$_2$CHF$_2$ | 3,5-Cl$_2$ | m.p.: 69–70° C. |
| 1.8 | 4-OCHF$_2$ | 2-methyl | m.p.: 53–54° C. |
| 1.9 | 4-OCF$_2$CHF$_2$ | 3-methyl | oil |
| 1.10 | 4-OCF$_2$CHClF | 3,5-Cl$_2$ | m.p.: 53–54° C. |
| 1.11 | 4-OCF$_2$CHFCF$_3$ | 3-Cl | m.p.: 53–54° C. |
| 1.12 | 4-OCF$_2$CHFCF$_3$ | 2,5-F$_2$ | $n_D^{23}$: 1.4381 |
| 1.13 | 4-OCF$_2$CF$_2$CF$_3$ | 2,5-Cl$_2$ | wax |
| 1.14 | 4-OCF$_2$CHF$_2$ | 3-Cl | m.p.: 52–53° C. |
| 1.15 | 4-OCHF$_2$ | 3-Cl | oil |
| 1.16 | 3-OCF$_3$ | n = 0 | $n_D^{23}$: 1.4680 |
| 1.17 | 3-OCF$_2$CHF$_2$ | n = 0 | $n_D^{22}$: 1.4669 |
| 1.18 | 2-OCF$_3$ | n = 0 | $n_D^{23}$: 1.4627 |
| 1.19 | 4-O—CH$_2$—CH=CHCl | 3,5-Cl$_2$ | m.p.: 89–90° C. |

TABLE 2

Compounds of formula

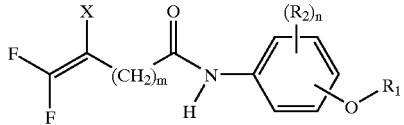

| Example No. | X | m | O—R$_1$ | $(R_2)_n$ |
|---|---|---|---|---|
| 2.1 | H | 3 | 4-OCHF$_2$ | n = 0 |
| 2.2 | H | 3 | 4-OCF$_3$ | 2-methyl |
| 2.3 | H | 3 | 4-OCClF$_2$ | n = 0 |
| 2.4 | H | 3 | 4-OCClF$_2$ | 2-methyl |
| 2.5 | H | 3 | 4-OCBrF$_2$ | n = 0 |
| 2.6 | H | 3 | 4-OCBrF$_2$ | 2-methyl |
| 2.7 | H | 3 | 4-OCF$_2$CHClF | 2-isopropyl |
| 2.8 | H | 3 | 4-OCF$_2$CHClF | 3-methyl |
| 2.9 | H | 3 | 4-OCF$_2$CHClF | 2,3,5-F$_3$ |
| 2.10 | H | 3 | 4-OCF$_2$CHF$_2$ | 2,3,5-F$_3$ |
| 2.11 | H | 3 | 4-OCBrF$_2$ | 2,3,5-F$_3$ |
| 2.12 | H | 3 | 4-OCBrF$_2$ | 2-isopropyl |
| 2.13 | H | 3 | 3-OCF$_2$CHClF | 4-methyl |
| 2.14 | H | 3 | 3-OCF$_2$CHF$_2$ | 4-methyl |
| 2.15 | H | 3 | 3-OCHF$_2$ | 4-methyl |
| 2.16 | H | 3 | 3-OCBrF$_2$ | 4-methyl |
| 2.17 | H | 3 | 3-OCF$_2$CHClF | 4-Cl |
| 2.18 | H | 3 | 3-OCF$_2$CHF$_2$ | 4-Cl |
| 2.19 | H | 3 | 3-OCF$_2$CHClF | 4-Br |
| 2.20 | H | 3 | 3-OCF$_2$CHF$_2$ | 4-Br |
| 2.21 | H | 3 | 3-OCF$_2$CHClF | n = 0 |
| 2.22 | H | 3 | 3-OCHF$_2$ | n = 0 |
| 2.23 | H | 3 | 2-OCF$_2$CHClF | n = 0 |
| 2.24 | H | 3 | 2-OCF$_2$CHF$_2$ | n = 0 |
| 2.25 | H | 3 | 3-OCBrF$_2$ | n = 0 |
| 2.26 | methyl | 3 | 4-OCF$_2$CHF$_2$ | n = 0 |
| 2.27 | methyl | 3 | 4-OCF$_2$CHF$_2$ | 2-methyl |
| 2.28 | methyl | 3 | 4-OCF$_2$CHF$_2$ | n = 0 |
| 2.29 | methyl | 3 | 4-OCF$_2$CHF$_2$ | 2-methyl |
| 2.30 | methyl | 3 | 4-OCF$_2$CHF$_2$ | 2-isopropyl |

TABLE 2-continued

Compounds of formula

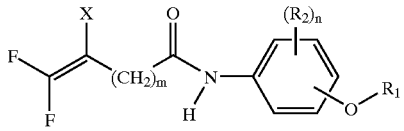

| Example No. | X | m | O—R$_1$ | $(R_2)_n$ |
|---|---|---|---|---|
| 2.31 | methyl | 3 | 4-OCBrF$_2$ | n = 0 |
| 2.32 | methyl | 3 | 4-OCBrF$_2$ | 2-methyl |
| 2.33 | methyl | 3 | 4-OCHF$_2$ | n = 0 |
| 2.34 | methyl | 3 | 4-OCHF$_2$ | 2-methyl |
| 2.35 | F | 3 | 4-OCF$_2$CHF$_2$ | n = 0 |
| 2.36 | F | 3 | 4-OCF$_2$CHF$_2$ | 2-methyl |
| 2.37 | F | 3 | 4-OCF$_2$CHF$_2$ | n = 0 |
| 2.38 | F | 3 | 4-OCF$_2$CHF$_2$ | 2-methyl |
| 2.39 | F | 3 | 4-OCF$_2$CHF$_2$ | 2-isopropyl |
| 2.40 | F | 3 | 4-OCBrF$_2$ | n = 0 |
| 2.41 | F | 3 | 4-OCBrF$_2$ | 2-methyl |
| 2.42 | F | 3 | 4-OCHF$_2$ | n = 0 |
| 2.43 | F | 3 | 4-OCHF$_2$ | 2-methyl |
| 2.44 | H | 5 | 4-OCF$_2$CHClF | n = 0 |
| 2.45 | H | 5 | 4-OCF$_2$CHClF | 2-methyl |
| 2.46 | H | 5 | 4-OCF$_2$CHClF | 2-isopropyl |
| 2.47 | H | 5 | 4-OCF$_2$CHF$_2$ | n = 0 |
| 2.48 | H | 5 | 4-OCF$_2$CHF$_2$ | 2-methyl |
| 2.49 | H | 5 | 4-OCHF$_2$ | n = 0 |
| 2.50 | H | 5 | 4-OCHF$_2$ | 2-methyl |
| 2.51 | H | 5 | 4-OCBrF$_2$ | n = 0 |
| 2.52 | H | 5 | 4-OCBrF$_2$ | 2-methyl |
| 2.53 | H | 5 | 4-OCF$_3$ | n = 0 |
| 2.54 | H | 5 | 4-OCF$_3$ | 2-methyl |
| 2.55 | H | 5 | 3-OCF$_2$CHClF | n = 0 |
| 2.56 | H | 5 | 3-OCF$_2$CHClF | 4-methyl |
| 2.57 | H | 5 | 3-OCF$_2$CHF$_2$ | n = 0 |
| 2.58 | H | 5 | 3-OCF$_2$CHF$_2$ | 4-methyl |
| 2.59 | H | 5 | 2-OCF$_2$CHClF | n = 0 |
| 2.60 | H | 5 | 2-OCF$_2$CHF$_2$ | n = 0 |
| 2.61 | H | 7 | 4-OCF$_2$CHClF | n = 0 |
| 2.62 | H | 7 | 4-OCF$_2$CHClF | 2-methyl |
| 2.63 | H | 7 | 4-OCF$_2$CHClF | 2-isopropyl |
| 2.64 | H | 7 | 4-OCF$_2$CHF$_2$ | n = 0 |
| 2.65 | H | 7 | 4-OCF$_2$CHF$_2$ | 2-methyl |
| 2.66 | H | 7 | 4-OCHF$_2$ | n = 0 |
| 2.67 | H | 7 | 4-OCHF$_2$ | 2-methyl |
| 2.68 | H | 7 | 4-OCBrF$_2$ | n = 0 |
| 2.69 | H | 7 | 4-OCBrF$_2$ | 2-methyl |
| 2.70 | H | 7 | 4-OCF$_3$ | n = 0 |
| 2.71 | H | 7 | 4-OCF$_3$ | 2-methyl |
| 2.72 | H | 7 | 3-OCF$_2$CHClF | n = 0 |
| 2.73 | H | 7 | 3-OCF$_2$CHClF | 4-methyl |
| 2.74 | H | 7 | 3-OCF$_2$CHF$_2$ | n = 0 |
| 2.75 | H | 7 | 3-OCF$_2$CHF$_2$ | 4-methyl |
| 2.76 | H | 7 | 2-OCF$_2$CHF$_2$ | n = 0 |
| 2.77 | H | 7 | 2-OCF$_2$CHF$_2$ | n = 0 |
| 2.78 | H | 9 | 4-OCF$_2$CHClF | n = 0 |
| 2.79 | H | 9 | 4-OCF$_2$CHClF | 2-methyl |
| 2.80 | H | 9 | 4-OCF$_2$CHClF | 2-isopropyl |
| 2.81 | H | 9 | 4-OCF$_2$CHF$_2$ | n = 0 |
| 2.82 | H | 9 | 4-OCF$_2$CHF$_2$ | 2-methyl |
| 2.83 | H | 9 | 4-OCHF$_2$ | n = 0 |
| 2.84 | H | 9 | 4-OCHF$_2$ | 2-methyl |
| 2.85 | H | 9 | 4-OCBrF$_2$ | n = 0 |
| 2.86 | H | 9 | 4-OCBrF$_2$ | 2-methyl |
| 2.87 | H | 9 | 4-OCF$_3$ | n = 0 |
| 2.88 | H | 9 | 4-OCF$_3$ | 2-methyl |
| 2.89 | H | 9 | 3-OCF$_2$CHClF | n = 0 |
| 2.90 | H | 9 | 3-OCF$_2$CHClF | 4-methyl |
| 2.91 | H | 9 | 3-OCF$_2$CHF$_2$ | n = 0 |
| 2.92 | H | 9 | 3-OCF$_2$CHF$_2$ | 4-methyl |
| 2.93 | H | 9 | 2-OCF$_2$CHClF | n = 0 |
| 2.94 | H | 9 | 2-OCF$_2$CHF$_2$ | n = 0 |
| 2.95 | H | 1 | 4-OCF$_2$CHClF | n = 0 |
| 2.96 | H | 1 | 4-OCF$_2$CHClF | 2-methyl |

TABLE 2-continued

Compounds of formula $$\begin{array}{c} X \\ F \\ \diagdown \\ F \end{array} C = C(CH_2)_m - \underset{H}{N} - \text{(aryl with } (R_2)_n \text{ and } O-R_1\text{)}$$

| Example No. | X | m | O—R$_1$ | (R$_2$)n |
|---|---|---|---|---|
| 2.97 | H | 1 | 4-OCF$_2$CHClF | 2-isopropyl |
| 2.98 | H | 1 | 4-OCF$_2$CHF$_2$ | n = 0 |
| 2.99 | H | 1 | 4-OCF$_2$CHF$_2$ | 2-methyl |
| 2.100 | H | 1 | 4-OCHF$_2$ | n = 0 |
| 2.101 | H | 1 | 4-OCHF$_2$ | 2-methyl |
| 2.102 | H | 1 | 4-OCBrF$_2$ | n = 0 |
| 2.103 | H | 1 | 4-OCBrF$_2$ | 2-methyl |
| 2.104 | H | 1 | 4-OCF$_3$ | n = 0 |
| 2.105 | H | 1 | 4-OCF$_3$ | 2-methyl |
| 2.106 | H | 1 | 3-OCF$_2$CHClF | n = 0 |
| 2.107 | H | 1 | 3-OCF$_2$CHClF | 4-methyl |
| 2.108 | H | 1 | 3-OCF$_2$CHF$_2$ | n = 0 |
| 2.109 | H | 1 | 3-OCF$_2$CHF$_2$ | 4-methyl |
| 2.110 | H | 1 | 2-OCF$_2$CHClF | n = 0 |
| 2.111 | H | 1 | 2-OCF$_2$CHF$_2$ | n = 0 |
| 2.112 | H | 3 | 4-O—CH$_2$—CH=CHCl | n = 0 |
| 2.113 | H | 3 | 4-O—CH$_2$—CH=CHCl | 2-CH$_3$ |
| 2.114 | H | 3 | 4-O—CH$_2$—CH=CHCl | 3-CH$_3$ |
| 2.115 | H | 3 | 4-O—CH$_2$—CH=CHCl | 2-isopropyl |
| 2.116 | H | 3 | 4-O—CH$_2$—CH=CHCl | n = 0 |
| 2.117 | H | 3 | 4-O—CH$_2$—CH=CHCl | 2-CH$_3$ |
| 2.118 | H | 3 | 4-O—CH$_2$—CH=CHCl | 3-CH$_3$ |
| 2.119 | H | 3 | 4-O—CH$_2$—CH=CHCl | 2-isopropyl |
| 2.120 | H | 3 | 4-O—CH$_2$—CH=CHCl | 3-Cl |
| 2.121 | H | 3 | 4-O—CH$_2$—CH=CHCl | n = 0 |
| 2.122 | H | 3 | 4-O—CH$_2$—CH=CHCl | n = 0 |
| 2.123 | H | 3 | 4-O—CH$_2$—CH≡CH | n = 0 |

Formulation Examples (%=percent by weight)

| Example F1: Emulsifiable concentrates | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Mixing together finely ground active ingredient and additives gives an emulsifiable concentrate which yields emulsions of the desired concentration on dilution with water.

| Example F2: Solutions | a) | b) | c) | d) |
|---|---|---|---|---|
| active ingredient | 80% | 10% | 5% | 95% |
| ethylene glycol monomethyl ether | 20% | — | — | — |
| polyethylene glycol (MW 400) | — | 70% | — | — |
| N-methylpyrrolid-2-one | — | 20% | — | — |
| epoxidised coconut oil | — | — | 1% | 5% |
| petroleum fraction (boiling range: 160–190°) | — | — | 94% | — |

Mixing together finely ground active ingredient and additives gives a solution which is suitable for use in the form of microdrops.

| Example F3: Granules | a) | b) | c) | d) |
|---|---|---|---|---|
| active ingredient | 5% | 10% | 8% | 21% |
| kaolin | 94% | — | 79% | 54% |
| highly disperse silicic acid | 1% | — | 13% | 7% |
| attapulgite | — | 90% | — | 18% |

The active ingredient is dissolved in dichloromethane, the solution is applied to the carrier mixture by spraying and the solvent is evaporated off in vacuo.

BIOLOGICAL EXAMPLES

Example B1

Ovicidal Action against *Heliothis virescens*

Egg deposits of *Heliothis virescens* on filter paper are immersed for a short time in an aqueous acetone test solution comprising 400 ppm of the test compound. After the test solution has dried, the eggs are incubated in petri dishes. 6 days later the percentage of eggs that have hatched is evaluated in comparison with untreated controls (% reduction in hatching rate).

The compounds from the Tables exhibit a good activity against *Heliothis virescens* in this test. In particular, compounds Nos. 1.1, 1.2, 1.3, 1.4, 1.5, 1.6, 1.7, 1.8, 1.9, 1.10, 1.16, 1.17 and 1.18 are more than 80% effective.

Example 2

*Nilaparvata lugens*

Rice plants are treated with an aqueous emulsion spray mixture comprising 400 ppm of the test compound. After the spray-coating has dried, the rice plants are populated with *Nilaparvata lugens* larvae in the 2nd and 3rd stages. The evaluation is carried out 21 days later. The percentage reduction in population (% activity) is determined by comparing the number of surviving cicadas on the treated plants with that on the untreated plants.

The compounds from the Tables exhibit a good activity against *Nilaparvata lugens* in this test. In particular, compounds 1.2, 1.4, 1.5, 1.8, 1.9, 1.11, 1.12 and 1.17 are more than 80% effective.

Example 3

Action against *Diabrotica balteata* Larvae

Maize seedlings are sprayed with an aqueous emulsion spray mixture comprising 400 ppm of the test compound. After the spray-coating has dried, the maize seedlings are populated with 10 *Diabrotica balteata* larvae in the second stage and then placed in a plastics container. The evaluation is carried out 6 days later. The percentage reduction in population (% activity) is determined by comparing the number of dead larvae on the treated plants with that on the untreated plants.

The compounds from the Tables exhibit a good activity against *Diabrotica balteata* in this test. In particular, compounds Nos. 1.1 to 1.18 are more than 80% effective.

Example 4

Action against *Tetranychus urticae*

Young bean plants are populated with a mixed population of *Tetranychus urticae* and sprayed one day later with an aqueous emulsion spray mixture comprising 400 ppm of the test compound. The plants are then incubated for 6 days at 25° C. and subsequently evaluated. The percentage reduction in population (% activity) is determined by comparing the number of dead eggs, larvae and adults on the treated plants with that on the untreated plants.

The compounds from the Tables exhibit a good activity against *Tetranychus urticae* in this test. In particular, compounds Nos. 1.1 to 1.13 and 1.17 are more than 80% effective.

Example 5

Action against *Spodoptera littoralis* L1

Young soybean plants are sprayed with an aqueous emulsion spray mixture comprising 400 ppm of the test compound. After the spray-coating has dried, the soybean plants are populated with 10 caterpillars of *Spodoptera littoralis* in the third stage and then placed in a plastics container. The evaluation is carried out 3 days later. The percentage reduction in population and the percentage reduction in feeding damage (% activity) are determined by comparing the number of dead caterpillars and the feeding damage on the treated plants with that on the untreated plants.

The compounds from the Tables exhibit good activity against *Spodoptera littoralis* in this test. In particular, compounds 1.1 to 1.17 are more than 80% effective.

Example 6

Action against *Aphis craccivora*

Pea seedlings are infested with *Aphis craccivora*, subsequently sprayed with a spray mixture comprising 400 ppm of the test compound and incubated at 20° C. The evaluation is carried out 3 and 6 days later. The percentage reduction in population (% activity) is determined by comparing the number of dead aphids on the treated plants with that on the untreated plants.

The compounds from Table 1 exhibit a good activity against *Aphis craccivora* in this test. In particular, compounds Nos. 1.1, 1.3, 1.4, 1.5, 1.8, 1.9 and 1.17 are more than 80% effective.

Example 7

Systemic Action against *Myzus persicae*

Pea seedlings are infested with *Myzus persicae,* and then placed with their roots in a spray mixture comprising 400 ppm of the test compound and incubated at 20° C. The evaluation is carried out 3 and 6 days later. The percentage reduction in population (% activity) is determined by comparing the number of dead aphids on the treated plants with that on the untreated plants.

The compounds from the Tables exhibit a good activity against *Myzus persicae* in this test. In particular, compound 1.3 is more than 80% effective.

What is claimed is:

1. A compound of formula

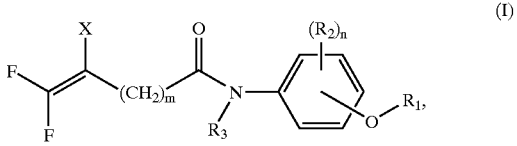

wherein $R_1$ is halo-$C_1$–$C_6$alkyl; halo-$C_2$–$C_6$alkenyl; or halo-$C_3$–$C_6$alkynyl;

$R_2$ is halogen, nitro, cyano, $C_1$–$C_{10}$alkyl, $C_2$–$C_6$alkenyl, $C_2$–$C_6$alkynyl, $C_3$–$C_8$cycloalkyl, $C_1$–$C_6$alkoxy, $C_3$–$C_6$alkenyloxy, halo-$C_1$–$C_{10}$alkyl, halo-$C_2$–$C_6$alkenyl, halo-$C_1$–$C_6$alkoxy, $C_3$–$C_6$alkynyloxy, $C_1$–$C_4$alkylthio, di($C_1$–$C_4$-alkyl)amine in which the two alkyl groups are independent of one another; aryl, aryloxy, arylthio, or substituted aryl, aryloxy or arylthio;

$R_3$ is hydrogen or unsubstituted or substituted $C_1$–$C_{10}$alkyl; or benzyl in which the phenyl ring is unsubstituted or monosubstituted by a substituent selected from the group consisting of nitro, halogen, —$CF_3$, —CN and $C_1$–$C_4$alkyl;

m is 3, 5, 7 or 9;

n is 0, 1, 2, 3 or 4; and

X is hydrogen;

in free form or in salt form.

2. A compound according to claim 1 of formula (I) in free form.

3. A compound according to claim 1 of formula (I), wherein $R_1$ is halo-$C_1$–$C_3$alkyl or halo-$C_3$–$C_6$alkenyl.

4. A compound according to claim 1 of formula (I), wherein $R_2$ is halogen or $C_1$–$C_4$alkyl.

5. A pesticidal composition that comprises as active ingredient at least one compound according to claim 1 of formula (I), in free form or, where applicable, in agrochemically suitable salt form, and at least one adjuvant.

6. A method or preparing a composition as described in claim 5, which comprises intimately mixing the active ingredient with the adjuvant(s).

7. A method of controlling pests, which comprises applying as active ingredient to the pests or to the habitat thereof a compound according to claim 1 of formula (I), in free form or, where applicable, in agrochemically suitable salt form.

* * * * *